United States Patent [19]
Chen et al.

[11] Patent Number: 5,965,533
[45] Date of Patent: Oct. 12, 1999

[54] ATRIAL NATRIURETIC PEPTIDE (ANP) AS AN ADDITIVE TO PERITONEAL DIALYSIS SOLUTIONS

[75] Inventors: Chi J. Chen, Hawthorn Woods; Ty R. Shockley, Highland Park, both of Ill.; Miles G. Johnston, 1517 Rawlings Dr., Pickering, Ontario, Canada, L1V 5A6

[73] Assignees: Baxter International Inc., Deerfield, Ill.; Miles G. Johnston, Toronto, Canada

[21] Appl. No.: 08/862,480

[22] Filed: May 23, 1997

[51] Int. Cl.$^6$ .............................. A61K 38/00; C07K 5/00; C07K 7/00; A01N 59/08
[52] U.S. Cl. .................................. 514/12; 514/2; 424/678
[58] Field of Search ................................ 424/678; 514/2, 514/12

[56] References Cited

U.S. PATENT DOCUMENTS

| | | |
|---|---|---|
| 5,258,368 | 11/1993 | Lewicki et al. . |
| 5,589,197 | 12/1996 | Shockley et al. ........................ 424/663 |
| 5,629,025 | 5/1997 | Shockley et al. ........................ 424/680 |
| 5,631,025 | 5/1997 | Shockley et al. ........................ 424/678 |

FOREIGN PATENT DOCUMENTS

| | | |
|---|---|---|
| 8900428 | 7/1988 | WIPO . |
| WO 89/00428 | 7/1988 | WIPO . |

OTHER PUBLICATIONS

Laffi et al., "Renal Hemodynamic and Natriuretic Effects of Human Atrial Natriuretic Factor Infusion in Cirrhosis With Ascites," Gastroenterology, vol. 96, Jan. 1989, pp. 167–177.

Bianciotti, L.G., et al.: "Atrial natiruretic factor increases peritoneal dialysis efficiency in nephrectomized rats." Peptides, (1996) 17 (1) 87–92, XP002081185, see the whole document.

Wang, T., et al.: "Atrial natriuretic factor increases peritoneal fluid removal." 15th Annual Meeting of the International Society of Blood Purification, Florence, Italy, Sep. 11–13, 1997. Blood Purification 15 (Suppl. 2), 1997, 4, XP002081186, see the whole document.

Wang, T. (Reprint), et al.: "Atrial natriuretic factor increases peritoneal fluid removal." Journal of the American Society of Nephrology, (Sep. 1997) vol. 8, Supp. S!, P 183A, XP002081187, see abstract AO856.

Teitze et al. "Renal haemodynamic changes, renal tubular function, sodium and water homeostatic hormones in patients with chronic glomerulonephritis and in healthy humans after intravenous infusion of amino acids", *Nephrol Dial Transplant (England)*, 1994, vol. 9, pp. 499–504.

Eiskjaer et al., "Dose–response study of atrial natriuretic peptide bolus injection in healthy man", *Eur. J Clim Invest (England)*, vol. 23, Jan. 1993, pp. 37–45.

Trevisan, et al., "Effects of atrial natriuretic peptide infusion on kidney function in normotensive type 1 (insulin dependent) diabetic patients before and after enalapril treatment", *J Hypertens Suppl (England)*, vol. 9, Dec. 1991, pp. 390–391.

Predel, et al., "Atrial natriuretic peptide in patients with essential hypertension. Hemodynamic, renal, and hormonal responses", *Am J. Hypertens (United States)*, vol. 4, Nov. 1991, pp. 871–879.

Hirata, et al., "Nephrogenous cyclic GMP production during NaCl loading and ANP infusion", *Jpn Heart J (Japan)*, vol. 31, Nov. 1990, pp. 809–816.

Gaillard, et al., "Renal response to infusion versus repeated bolus injections of atrial natriuretic factor in man", *Eur J Clin Pharmacol (Germany, West)*, vol. 36, 1989, pp. 195–197.

Laffi et al., "Renal hemodyamic and natriuretic effects of human atrial natriuretic factor infusion in cirrhosis with ascites", *Gastroenterology (United States)*, vol. 96, Jan. 1989, pp. 167–177.

Cottier, et al., "Renal response to low–dose infusion of atrial natriuretic peptide in normal man", *Kidney Int Suppl (United States)*, vol. 25, Sep. 1988, pp. 72–78.

Biollaz, et al., "Site of the action of a synthetic atrial natriuretic peptide evaluated in humans", *Kidney Int (United States)*, vol. 32, Oct. 1987, pp. 537–546.

*Primary Examiner*—Avis M. Davenport
*Attorney, Agent, or Firm*—Thomas S. Borecki; Charles R. Mattenson; Robert M. Barrett

[57] ABSTRACT

The present invention provides a peritoneal dialysis solution that contains atrial natriuretic peptide (ANP), a derivative of ANP, an analogue of ANP, a substance that binds ANP to clearance receptors or a substance that promotes ANP synthesis, which results in an increased net ultrafiltration and increased sodium clearance experienced in peritoneal dialysis patients.

20 Claims, 1 Drawing Sheet

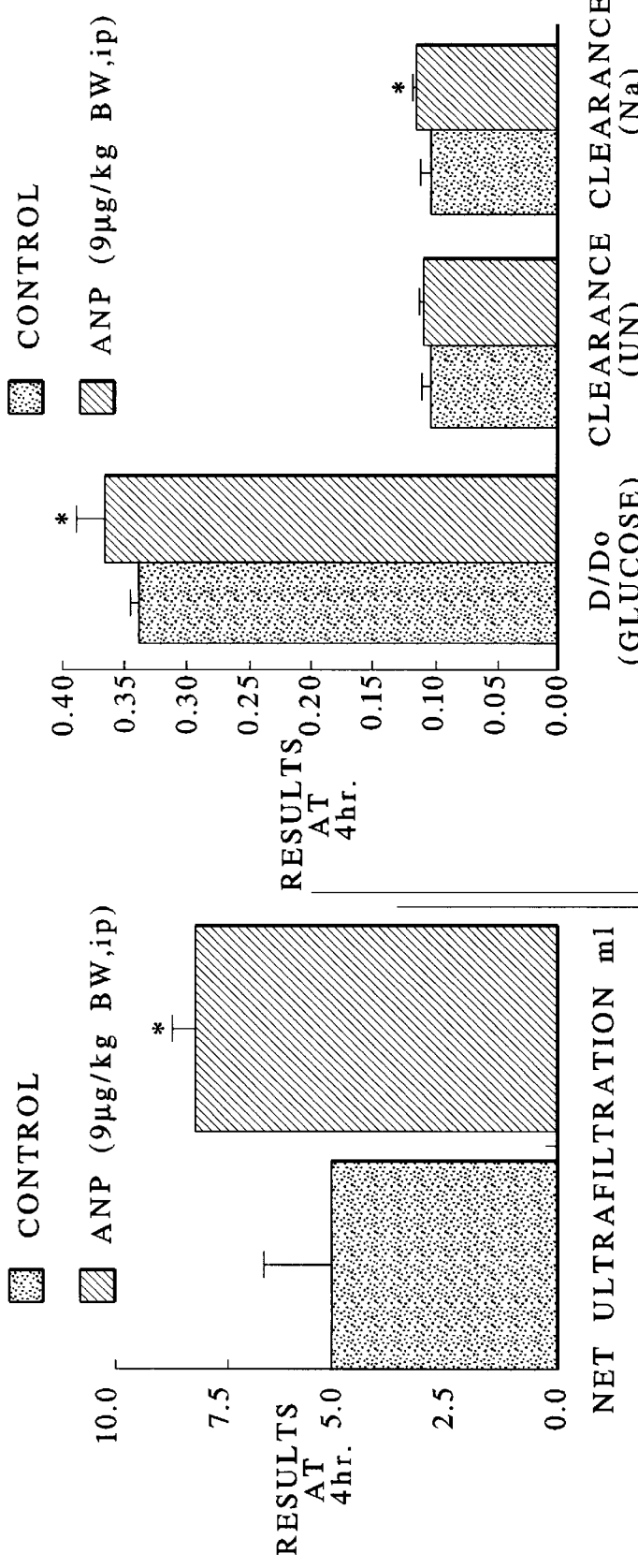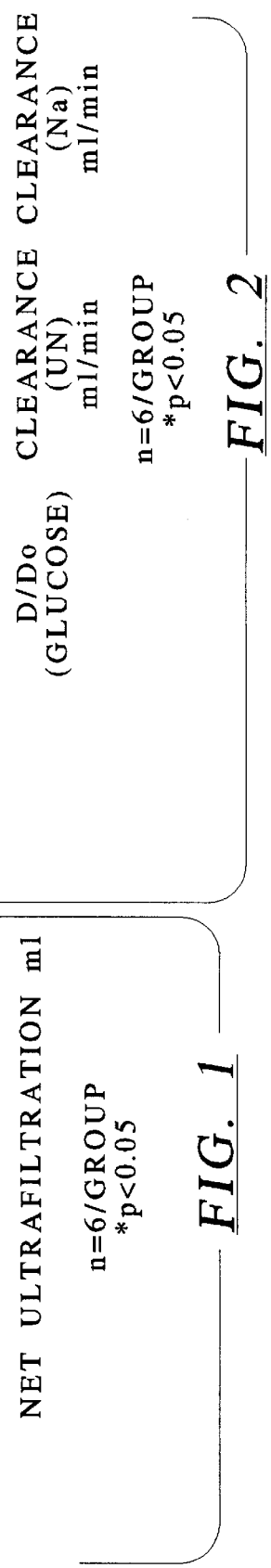

ATRIAL NATRIURETIC PEPTIDE (ANP) AS AN ADDITIVE TO PERITONEAL DIALYSIS SOLUTIONS

BACKGROUND OF THE INVENTION

The present invention relates generally to peritoneal dialysis and solutions for the same. More specifically, the present invention relates to the use of atrial natriuretic peptide (ANP) as an additive to peritoneal dialysis solutions to increase the adequacy thereof.

Atrial natriuretic peptide (ANP) is a biological hormone. ANP has also been referred to as atrial natriuretic factor (ANF). Its sequence and structure are known and its synthetic equivalent is commercially available in the form of α-H-ANP. ANP is synthesized primarily in the atrium of the heart as a prehormone that is cleaved to a prohormone of 126 amino acids. The principal circulating form of ANP has been designated as ANP (99–126). The amino terminal (ANP (1–98) fragment is processed into ANP (1–30) and ANP (31–67) fragments, both of which possess biological activity.

ANP has been infused intravenously in treating hypertension, heart disease, acute renal failure and edema. ANP, when infused intravenously, has been shown to increase the glomerular filtration rate (GFR) and filtration fraction. ANP has also been shown to reduce proximal tubule sodium ion concentration and water reabsorption. Further, ANP has been shown to inhibit net sodium ion reabsorption and water reabsorption in the collecting duct, lower plasma renin concentration and inhibit aldosterone secretion. Use of ANP intravenously has also resulted in mean arterial pressure reduction and has led to natriuresis and diuresis.

Dialysis provides a method for supplementing or replacing renal function in certain patients. Principally, hemodialysis and peritoneal dialysis are the two methods that are currently utilized.

In hemodialysis, the patient's blood is passed through an artificial kidney dialysis machine. A membrane in the machine acts as an artificial kidney for cleansing the blood. Because it is an extracorporeal treatment that requires special machinery, hemodialysis is fraught with certain inherent disadvantages such as the availability of dialysis machines and the possibility of infection and contamination.

To overcome the disadvantages associated with hemodialysis, peritoneal dialysis was developed. Peritoneal dialysis utilizes the patient's own peritoneum as a semipermeable membrane. The peritoneum is a membranous lining of the abdominopelvic walls of the body. The peritoneum is capable of acting as a natural semi-permeable membrane because of its large number of blood vessels and capillaries.

In operation, a peritoneal dialysis solution is introduced into the peritoneal cavity utilizing a catheter. After a sufficient period of time, an exchange of solutes between the dialysate and blood is achieved. Fluid removal is achieved by providing a suitable osmotic gradient from the dialysate to the blood to permit water outflow from the blood. This allows the proper acid-base, electrolyte and fluid balance to be achieved in the blood. After an appropriate dwell period, the dialysis solution or dialysate is drained from the body through a catheter.

While peritoneal dialysis provides some advantages over hemodialysis, primary disadvantages of peritoneal dialysis include an insufficient net ultrafiltration and insufficient clearances of urea nitrogen and sodium. As a result, overall peritoneal dialysis adequacy can be insufficient. Therefore, there is a need for an improved peritoneal dialysis solution which provides a greater net ultrafiltration and increased clearances of components such as urea nitrogen.

SUMMARY OF THE INVENTION

The present invention provides an improved peritoneal dialysis solution that includes an additive in the form of atrial natriuretic peptide (ANP), an ANP derivative, an ANP analogue, a substance that binds to ANP clearance receptors and therefore reduces the clearance of ANP and/or a promoter of ANP synthesis. A peritoneal dialysis solution made in accordance with the present invention improves the adequacy of the peritoneal dialysis conducted with the solution of the present invention. When the term ANP is used below, it is intended to encompass the ANP prohormone molecule, the circulating form of ANP as well as the fragments having biological activity. The sequence of natural ANP in the human body is identified as SEQ ID NO:1.

In an embodiment, the dialysis solution of the present invention comprises 0.1 $\mu$g/L - 50 mg/L ANP.

In an embodiment, the dialysis solution of the present invention comprises from about 16.7 $\mu$g/L to about 5 mg/L.

In an embodiment, the dialysis solution of the present invention comprises a concentration of ANP so that the patient receives a dose of ANP ranging from 0.01 $\mu$g/kg BW to 1 mg/kg BW.

In an embodiment, the dialysis solution of the present invention comprises a concentration of ANP so that the patient receives a dose of ANP ranging from about 1 $\mu$g/kg BW to about 100 $\mu$g/kg BW.

In an embodiment, the concentration of ANP in the dialysis solution ranges from about $3.3 \times 10^{-5}$ $\mu$mol/L to about 16 $\mu$mol/L.

In an embodiment, the dialysis solution of the present invention further comprises from about 1.5% to about 4.25% dextrose.

In an embodiment, the peritoneal dialysis solution of the present invention comprises an amount of ANP sufficient to increase the net ultrafiltration of the dialysis solution.

In an embodiment, the peritoneal dialysis solution of the present invention comprises an amount of ANP sufficient to increase the clearance of sodium.

In an embodiment, the peritoneal dialysis solution of the present invention comprises an amount of ANP sufficient to increase the clearance of phosphorus.

In an embodiment, the peritoneal dialysis solution of the present invention comprises an amount of ANP sufficient to increase the clearance of uremic toxins.

In an embodiment, the peritoneal dialysis solution of the present invention comprises an amount of ANP sufficient to increase the clearance of creatinine.

In an embodiment, the peritoneal dialysis solution of the present invention comprises an amount of ANP sufficient to increase the clearance of urea nitrogen.

The present invention also provides a method for improving the adequacy of a peritoneal dialysis solution which comprises the step of adding atrial natriuretic peptide (ANP), a derivative of ANP, an analogue of ANP, a substance that binds ANP to clearance receptors or a substance that promotes the synthesis of ANP, to the peritoneal dialysis solution.

In an embodiment of the method of the present invention, the ANP is present in the dialysis solution in a concentration ranging from about 0.1 μg/L to about 50 mg/L or a concentration which enables the patient to receive a dose of ANP ranging from about 0.01 μg/kg BW to about 1 mg/kg BW.

It is an advantage of the present invention to provide a peritoneal dialysis solution, which includes atrial natriuretic peptide (ANP), an ANP derivative, an ANP analogue, a substance that binds ANP to clearance receptors and/or a substance that promotes the synthesis of ANP, that results in an improved net ultrafiltration in a peritoneal dialysis patient.

Another advantage of the present invention is that it provides a peritoneal dialysis solution that results in an improved clearance of sodium in a peritoneal dialysis patient.

Another advantage of the present invention is that it provides a peritoneal dialysis solution that results in an improved clearance of urea nitrogen in a peritoneal dialysis patient.

Another advantage of the present invention is that it provides a peritoneal dialysis solution that results in an improved clearance of phosphorous in a peritoneal dialysis patient.

Another advantage of the present invention is that it provides a peritoneal dialysis solution that results in an improved clearance of uremic toxins in a peritoneal dialysis patient.

Another advantage of the present invention is that it provides a peritoneal dialysis solution that results in an improved clearance of creatinine in a peritoneal dialysis patient.

Additional features and advantages of the present invention are described in, and will be apparent from, the detailed description of the presently preferred embodiments.

BRIEF DESCRIPTION OF THE DRAWINGS

FIG. 1 illustrates, graphically, the net ultrafiltration provided by a peritoneal dialysis solution of the present invention as compared to a conventional peritoneal dialysis solution.

FIG. 2 illustrates, graphically, the glucose absorption, urea nitrogen clearance and sodium clearance of the peritoneal dialysis solution of the present invention as compared to a conventional peritoneal dialysis solution.

DETAILED DESCRIPTION OF THE PRESENTLY PREFERRED EMBODIMENTS

The present invention provides a peritoneal dialysis solution that includes atrial natriuretic peptide (ANP) that is designed primarily to: (1) improve the net ultrafiltration experienced by peritoneal dialysis patients and (2) improve the clearance of sodium in peritoneal dialysis patients. Other benefits such as improved clearances of phosphorous, uremic toxins, urea nitrogen and creatinine may also be provided.

The peritoneal dialysis solution of the present invention preferably comprises a base solution which consists of a 1.5% dextrose peritoneal dialysis solution sold under the DIANEAL® trademark. ANP is added to the solution in an amount ranging from about 0.1 μg/L to about 50 mg/L or in a concentration which enables the patient to receive a dose of ANP ranging from about 0.01 μg/kg BW to about 1 mg/kg BW. The typical dialysis solution volume for a patient will range from 2 liters to 3 liters depending upon the patient's size and weight. Accordingly, the ANP concentration may need to be adjusted.

Overall, the dose of ANP administered to the peritoneal dialysis patient should range from 0.01 μg/kg BW to 1 mg/kg BW and preferably from about 1 μg/kg BW to about 100 μg/kg BW. In terms of concentration, the dialysis solution can contain from about 0.1 μg/L to about 50 mg/L ANP and more preferably from about 16.7 μg/L to about 5 mg/L ANP. The dwell time is preferably about 4 hours but may range from 2 to 6 hours.

In an embodiment, the base dialysis solution includes 120–150 mEq/L sodium; 0.0–110 mEq/L chloride; 0.0–45.0 mEq/L lactate; 0.0–45.0 mEq/L bicarbonate; 0.0–4.0 mEq/L calcium; 0.0–4.0 mEq/L magnesium and 1.0–5.0% w/v dextrose as an osmotic agent. Dextrose may be combined with or substituted for another osmotic agent which may include amino acids, polypeptides, polyglucose and/or glycerol or other suitable osmotic agents. The osmolality of the base solution preferably ranges from 300 to 500 mOsm/kg.

In an embodiment, the base dialysis solution includes 120–150 mEq/L sodium, 75–110 mEq/L chloride, 15–40 mEq/L lactate, 0–40 mEq/L bicarbonate, 2.5–3.5 mEq/L calcium, 0.5–1.5 mEq/L magnesium and 1.5–4.25% w/v dextrose.

In an embodiment, instead of or in addition to ANP, an ANP derivative or analogue or a substance that binds to ANP clearance receptors or a promoter of ANP synthesis is utilized. Such ANP analogues including compounds with modified ANP sequences, ANP receptor agonists, and substances blocking ANP clearance can be found in U.S. Pat. Nos. 5,258,368; 5,512,455; 5,212,286; 5,449,662; 5,114,923; 4,764,504; 4,618,600; 5,106,834; 4,816,443; and 4,761,469; and foreign patent Nos. DE 3706731; EP 244169; EP 232078; EP 182984; WO 8900428; WO 9420534; EP 400227; and EP 371730.

Experimental Results

A first experiment was performed to assess the effect of intraperitoneal administered ANP on peritoneal dialysis transport characteristics in rats. In this study, a dose of 9 μg ANP/kg BW of rat was mixed in a base solution of 2.5% dextrose DIANEAL® solution. The rats were injected with 90 ml/kg BW of either the above solution with the ANP additive or an unaltered control DIANEAL® solution.

Blood samples were taken before and after the 4 hour dwell period. Dialysate samples were collected at the start of the dwell and every 2 hours thereafter. All samples were analyzed for urea nitrogen (UN), sodium (Na), glucose, protein (prtn), and osmolality (Osm). At the end of the 4 hour dwell period, the rats were sacrificed, the abdominal walls excised, and the effluents collected and weighed. The results of the samples collected at the 4 hour mark are summarized in Table 1.

TABLE 1

|  | Control | ANP |
| --- | --- | --- |
| nUF, ml | 5.10 ± 1.57 | 8.17 ± 0.52* |
| Osm, mOsm/kg | 304.8 ± 2.1 | 308.0 ± 3.5 |
| D/P (UN) | 0.87 ± 0.03 | 0.81 ± 0.04* |
| D/D$_0$ (glucose) | 0.337 ± 0.007 | 0.363 ± 0.024* |
| D/P (prtn) | 0.0104 ± 0.0012 | 0.0106 ± 0.0009 |
| Clearance (Na), ml/min | 0.0999 ± 0.008 | 0.1110 ± 0.0027* |
| Clearance (UN), ml/min | 0.101 ± 0.007 | 0.106 ± 0.005 |
| Clearance (prtn), μl/min | 1.214 ± 0.199 | 1.379 ± 0.117 |

(mean ± SD, *p < 0.05)

The pH of the control solution was 5.12 while the pH of the ANP solution was 5.10. The osmolality of the control solution was 391 while the osmolality of the ANP solution was 390.

To prepare the above ANP solution, 250 cc of DIANEAL® PD-2 solution was transferred into a 250 ml empty bag (VIAFLEX®). 10 cc of DIANEAL® PD-2 solution was injected into a vial containing 200 gg of ANF (atrial natriuretic factor—yANF,rat,28AA sold by Peninsula Laboratories, Inc.). 1.25 cc of the DIANEAL®/ANF solution was then withdrawn with a needle and syringe and injected into the 250 ml bag containing the DIANEAL® base solution through a 0.22 $\mu$m sterile filter. The bag was then enclosed with a sampling site coupler. The control solution was similarly transferred into a new 250 ml bag (VIAFLEX®) and enclosed with a sampling site coupler.

The results of Table 1 are also illustrated in FIGS. 1 and 2. As seen from Table 1 and FIGS. 1 and 2, the employment of ANP as an additive to a peritoneal dialysis solution increases the net ultrafiltration and sodium clearance.

In a second experiment performed on sheep, ANP was added to a 4.25% dextrose DIANEAL® solution to provide a final concentration of ANP in the solution of $1 \times 10^{31}$ $^7$M. The dialysis solution was then infused into the peritoneal cavity of the sheep in 50 ml/kg BW volumes. The dwell time periods were 6 hours; the sheep remained conscious. A summary of the results is presented in Table 2:

TABLE 2

|  | ANP (n = 5) | | Controls (n = 6) | |
| --- | --- | --- | --- | --- |
|  | mean | SEM | mean | SEM |
| weight | 24.60 | 0.74 | 25.33 | 0.76 |
| pl. vol. (ml/kg) | 52.70* | 3.90 | 58.11 | 1.82 |

TABLE 2-continued

|  | ANP (n = 5) | | Controls (n = 6) | |
| --- | --- | --- | --- | --- |
|  | mean | SEM | mean | SEM |
| Vo (ml/kg) | 50.41 | 0.47 | 50.66 | 0.46 |
| V6 (ml/kg) | 72.46* | 3.99 | 65.55 | 2.31 |
| NUF (ml/kg) | 22.05* | 3.77 | 14.86 | 2.55 |
| LFR (ml/kg) | 6.45* | 1.62 | 11.42 | 1.27 |
| Fl. loss (ml/kg) | 13.39 | 2.84 | 16.15 | 2.24 |
| Bl. rec. (%) | 11.69* | 2.51 | 19.37 | 2.29 |
| PC rec. (%) | 82.12 | 4.26 | 78.16 | 2.96 |
| Total rec. (%) | 93.81* | 2.62 | 97.54 | 1.52 |

*p < 0.05 wherein pl. vol. is plasma volume; Vo is the volume of the peritoneal cavity before the commencement of the dialysis; V6 is the volume of the peritoneal cavity after six hours; LFR is lymph flow rate; Bl. rec. is blood recovery; and PC rec. is peritoneal cavity recovery.

As can be seen above in Table 2, the net ultra filtration (NUF) increases substantially from a mean of 14.86 to a mean of 22.05 when ANP is added to the base solution.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An improved peritoneal dialysis solution comprising.

an osmotic agent; and atrial natriuretic peptide (ANP).

2. The solution of claim 1 wherein the ANP is present in an amount ranging from 0.1 μg to 50 mg per liter of dialysis solution.

3. The solution of claim 1 wherein the ANP is present in an amount ranging from 16.7 μg to 5 mg per liter of dialysis solution.

4. The solution of claim 1 wherein the solution comprises a sufficient amount of ANP to result in an increase in net ultrafiltration.

5. The solution of claim 1 wherein the solution comprises a sufficient amount of ANP to result in an increase in the clearance of sodium.

6. The solution of claim 1 wherein the solution comprises a sufficient amount of ANP to result in an increase in the clearance of urea nitrogen.

7. The solution of claim 1 wherein the solution comprises a sufficient amount of ANP to result in an increase in the clearance of uremic toxins.

8. The solution of claim 1 wherein the solution comprises a sufficient amount of ANP to result in an increase in the clearance of phosphorous.

9. The solution of claim 1 wherein the solution comprises a sufficient amount of ANP to result in an increase in the clearance of creatinine.

10. A peritoneal dialysis solution comprising from about:

120 to 150 (mEq/L) sodium;

0 to 110 (mEq/L) chloride;

0 to 45 (mEq/L) lactate;

0 to 45 (mEq/L) bicarbonate;

0 to 4.0 (mEq/L) calcium;

0 to 4.0 (mEq/L) magnesium;

an osmotic agent; and atrial natriuretic peptide (ANP).

11. A method of improving a peritoneal dialysis solution, the method comprising the following step:

adding atrial natriuretic peptide (ANP) and an osmotic agent to the peritoneal dialysis solution.

12. The method of claim 11 wherein the ANP is added to the solution in an amount ranging from 0.1 μg to 50 mg per liter of dialysis solution.

13. The method of claim 11 wherein the ANP is added to the solution in an amount ranging from 16.7 μg to 5 mg per liter of solution.

14. The method of claim 11 wherein the ANP is added in an amount sufficient to increase the net ultrafiltration of the peritoneal dialysis.

15. The method of claim 11 wherein the ANP is added in an amount sufficient to increase the clearance of sodium.

16. The method of claim 11 wherein the ANP is added in an amount sufficient to increase the clearance of uremic toxins.

17. The method of claim 11 wherein the ANP is added in an amount sufficient to increase the clearance of creatinine.

18. The method of claim 11 wherein the ANP is added in an amount sufficient to increase the clearance of phosphorous.

19. A method of performing peritoneal dialysis on a patient which results in an increased net ultrafiltration, the method comprising:

administering to the patient a peritoneal dialysis solution comprising a component selected from the group consisting of atrial natriuretic peptide (ANP), a substance that binds to ANP clearance receptors and a substance that promotes the synthesis of ANP.

20. An improved peritoneal dialysis solution comprising a component selected from the group consisting of:

an osmotic agent; and atrial natriuretic peptide (ANP), a substance that binds to ANP clearance receptors and a promoter of ANP synthesis.

* * * * *

UNITED STATES PATENT AND TRADEMARK OFFICE
CERTIFICATE OF CORRECTION

PATENT NO. : 5,965,533
DATED : October 12, 1999
INVENTOR(S) : Chi J. Chen, et al.

It is certified that error appears in the above-identified patent and that said Letters Patent is hereby corrected as shown below:

Column 5, Line 4: please delete "200 gg" and insert --200 μg-- therefor.

Column 5, Line 19: please delete "$1 \times 10^{31\ 7}M$" and insert --$1 \times 10^{-7}M$ -- therefor.

Signed and Sealed this

Seventeenth Day of October, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 125 amino acid residues
      (B) TYPE: amino acid
      (C) STRANDEDNESS: Not Relevant
      (D) TOPOLOGY: Not Relevant (ii) MOLECULE TYPE: peptide (xi) SEQUENCE DESCRIPTION: SEQ ID NO:1:

```
Asn Pro Met Tyr Asn Ala Val Ser Asn Ala Asp Leu Met Asp Phe Lys
                 5                  10                  15
Asn Leu Leu Asp His Leu Glu Glu Lys Met Pro Leu Glu Asp Glu Val
             20                  25                  30
Val Pro Pro Gln Val Leu Ser Glu Pro Asn Glu Glu Ala Ala Ala Leu
         35                  40                  45
Ser Pro Leu Pro Glu Val Pro Pro Trp Thr Gly Glu Val Ser Pro Ala
     50                  55                  60
Gln Arg Asp Gly Gly Ala Leu Gly Leu Gly Arg Gly Pro Trp Asp Ser
 65                  70                  75                  80
Ser Asp Arg Ser Ala Leu Leu Lys Leu Arg Ala Leu Leu Thr Ala Pro
                 85                  90                  95
```

-continued

```
Arg Ser Leu Arg Arg Ser Ser Cys Phe Gly Gly Arg Met Asp Arg Ile
            100             105             110

Gly Ala Gln Ser Gly Leu Gly Cys Asn Ser Phe Arg Tyr
            115             120             125
```